United States Patent
Kimura et al.

(10) Patent No.: US 9,068,932 B2
(45) Date of Patent: *Jun. 30, 2015

(54) SPECTROPHOTOMETER

(75) Inventors: Toshiro Kimura, Kyoto (JP); Tomoki Sasayama, Nagaokakyo (JP); Daijiro Kato, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 366 days.

This patent is subject to a terminal disclaimer.

(21) Appl. No.: 13/528,659

(22) Filed: Jun. 20, 2012

(65) Prior Publication Data

US 2012/0327411 A1    Dec. 27, 2012

(30) Foreign Application Priority Data

Jun. 21, 2011 (JP) .................. 2011-137302

(51) Int. Cl.
- G01J 3/42 (2006.01)
- G01N 21/33 (2006.01)
- G01N 21/27 (2006.01)

(52) U.S. Cl.
CPC .............. G01N 21/33 (2013.01); G01N 21/276 (2013.01)

(58) Field of Classification Search
USPC .................................. 356/317–319
See application file for complete search history.

(56) References Cited

U.S. PATENT DOCUMENTS

2013/0155405 A1 *  6/2013  Kimura et al. ................ 356/319

FOREIGN PATENT DOCUMENTS

JP    2002-162294    6/2002

* cited by examiner

*Primary Examiner* — Abdullahi Nur
(74) *Attorney, Agent, or Firm* — Morgan, Lewis & Bockius LLP (57) ABSTRACT

A spectrophotometer has a specimen cell; a light source unit for emitting light to the specimen cell; a photodetector for detecting the light that passed through the specimen cell; a light-shielding unit for blocking the light from impinging on the photodetector at predetermined periods; a memory unit for storing output strength signals detected by the photodetector; and a controller for calculating transmittance or absorbance based on output strength signal S of the incidence duration and output strength signal DS of the light-blocked duration stored in the memory unit. The incidence duration and light-blocked duration occur in this sequence in a single period. The controller calculates the true output strength signal $s_N$ of the $N^{th}$ period removed of the effects of output strength signal $S_{N-1}$ of the incidence duration of the $(N-1)^{th}$ period that are included in the output strength signal $S_N$ of the incidence duration of the $N^{th}$ period.

12 Claims, 8 Drawing Sheets

SPECTROPHOTOMETER

TECHNICAL FIELD

The present invention relates to a spectrophotometer and, in particular, to a double-beam and single-beam type ultraviolet-visible spectrophotometers.

BACKGROUND ART

Figure 11:
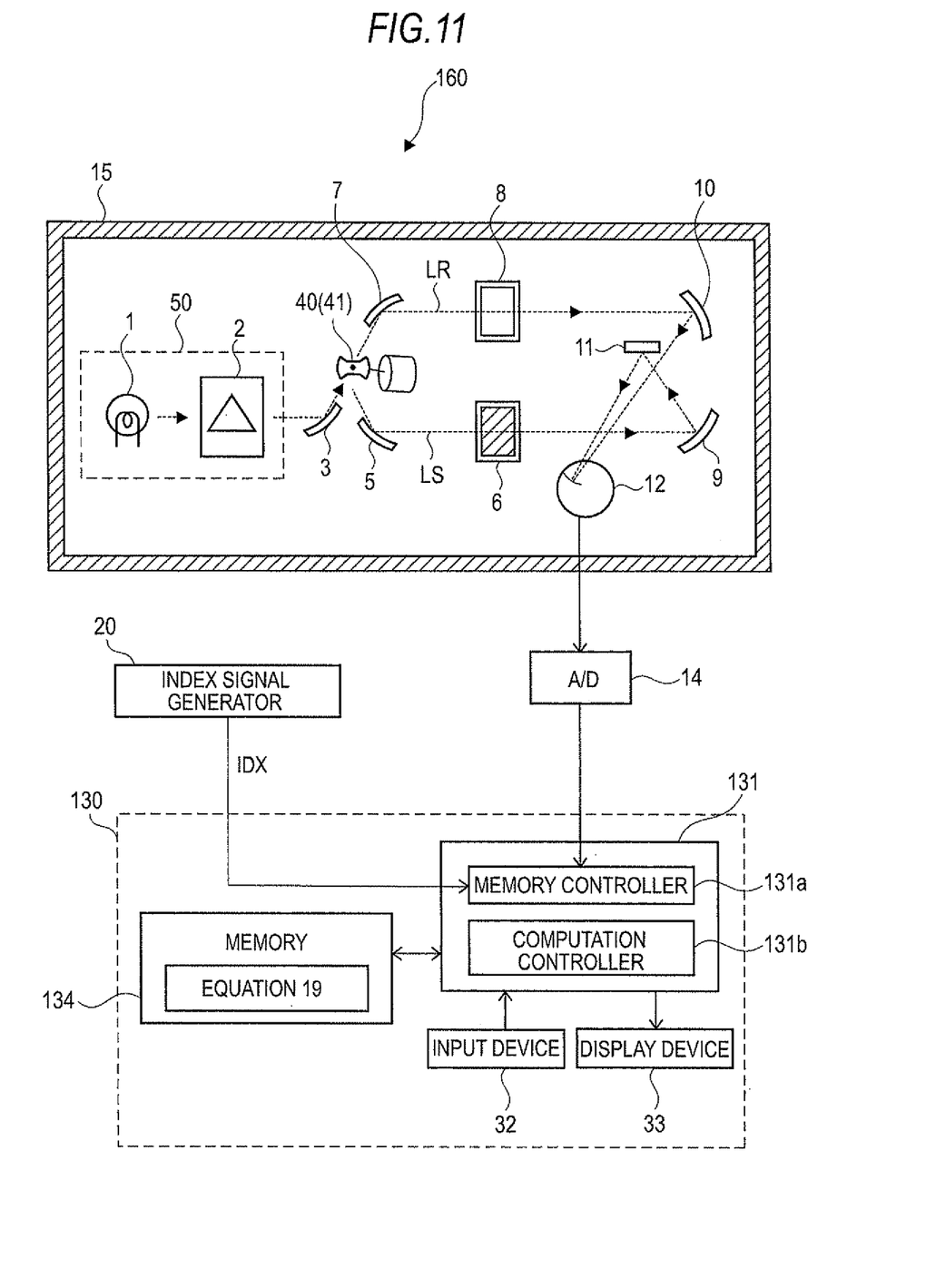
FIG. 11 shows a schematic view of the configuration of a previous double-beam type ultraviolet-visible spectrophotometer.

Double-beam type ultraviolet-visible spectrophotometers have been developed as a device for measuring the transmittance of specimens (e.g., see Patent Literature 1). FIG. 11 shows a schematic view of a double-beam type ultraviolet-visible spectrophotometer.

The ultraviolet-visible spectrophotometer 160 comprises: specimen cell 6; reference cell 8; light source unit 50 comprising spectrometer 2 and light source 1 that emits measurement light; photodetector 12; sector mirror (switching unit and light-shielding unit) 40; plurality of reflecting mirrors 3, 5, 7, 9, 10 and 11; enclosure 15 that does not allow light to pass through; index signal generator 20; analog/digital (A/D) converter 14; and computer 130 that controls the entire ultraviolet-visible spectrophotometer 160.

The specimen cell 6, reference cell 8, light source unit 50, photodetector 12, sector mirror (switching unit and light-shielding unit) 40 and reflecting mirrors 3, 5, 7, 9, 10 and 11 are disposed at predetermined positions inside enclosure 15.

A person performing an analysis can open a door provided in the enclosure 15 and replace the specimen cell 6 or reference cell 8 with a new specimen cell or a new reference cell.

Within light source unit 50, light emitted from light source 1 becomes incident to spectrometer 2 where monochromatic light (measurement light) of a desired wavelength $\lambda$, is extracted.

Sector mirror 40 alternately makes the monochromatic light into a specimen-side light beam LS or a reference-side light beam LR using a predetermined period. The sector mirror 40 is also provided with a light-shielding unit 41, which, as the sector mirror rotates, blocks the specimen-side light beam LS or reference-side light beam LR using a predetermined period and thereby creates alternating predetermined periods of specimen-side light beam LS incident duration and specimen-side light beam LS blocked duration and reference-side light beam LR incident duration and reference-side light beam LR blocked duration.

In synchrony with the rotation of sector mirror 40, which is rotatably driven at a predetermined speed, an index signal generator 20 generates index signal IDX at a rate of 1 pulse per rotation. As an example the rotational frequency of sector mirror 40 may be 50 Hz or 60 Hz in synchrony with the frequency of the power supply.

A computer 130 comprises a CPU (controller) 131 and memory (memory unit) 134. Further connected thereto are a display device 33 and an input device 32 comprising a keyboard, mouse and the like. To explain the functional blocks of the CPU 131, CPU 131 comprises a memory controller 31a for storing in memory 134 the output strength signal from a photodetector 12 and a computation controller 131b for calculating transmittance.

With an ultraviolet-visible spectrophotometer 160 such as the afore-described, light emitted by light source 1 becomes incident to spectrometer 2 where monochromatic light having a desired wavelength $\lambda$ is extracted. The monochromatic light is sent to sector mirror 40 via reflecting mirror 3 and is then alternately separated by sector mirror 40 into specimen-side light beam LS and reference-side light beam LR.

First, the specimen-side light beam LS is irradiated onto specimen cell 6 via reflecting mirror 5, and the light that passes through specimen cell 6 is sent to the light-receiving surface of photodetector 12 via reflecting mirrors 9 and 11. The light that is sent to photodetector 12 is photo-electrically converted by photodetector 1, which outputs output strength signal S during the specimen-side incidence duration. Furthermore, because sector mirror 40 is provided with a light-shielding unit 41, which, together with the rotation of sector mirror 40, blocks specimen-side light beam LS using a predetermined period, the output strength signal from photodetector 12 that corresponds to light-shielding unit 41 becomes output strength signal DS during the specimen-side light-blocked duration. The output strength signals S and DS of photodetector 12 are sampled by A/D converter 14 using a predetermined time interval and are converted into digital voltage values (signal values).

The reference-side light beam LR is irradiated onto reference cell 8 via reflecting mirror 7, and the light that passes through reference cell 8 is sent to the light-receiving surface of photodetector 12 via reflecting mirror 10. The light that is sent to photodetector 12 is photo-electrically converted by photodetector 12 and is extracted as output strength signal R for the reference-side incidence duration. Furthermore, because sector mirror 40 is provided with a light-shielding unit 41, which, together with the rotation of sector mirror 40, blocks reference-side light beam LR using a predetermined period, the output strength signal from photodetector 12 that corresponds to light-shielding unit 41 becomes output strength signal DR during the reference-side light-blocked duration. The output strength signals R and DR of photodetector 12 are sampled by A/D converter 14 using a predetermined time interval and are converted to digital voltage values (signal values).

The memory controller 31a of computer 130 controls the storage in memory 134 of signal values (output strength signals S, DS, R and DR) from photodetector 12. When doing this, the signal values are stored in association with when the output strength signal was obtained from the photodetector 12, that is, whether during the period when light was blocked by light-shielding unit 41 or during the period when the optical path was switched by sector mirror 40.

Figure 2:
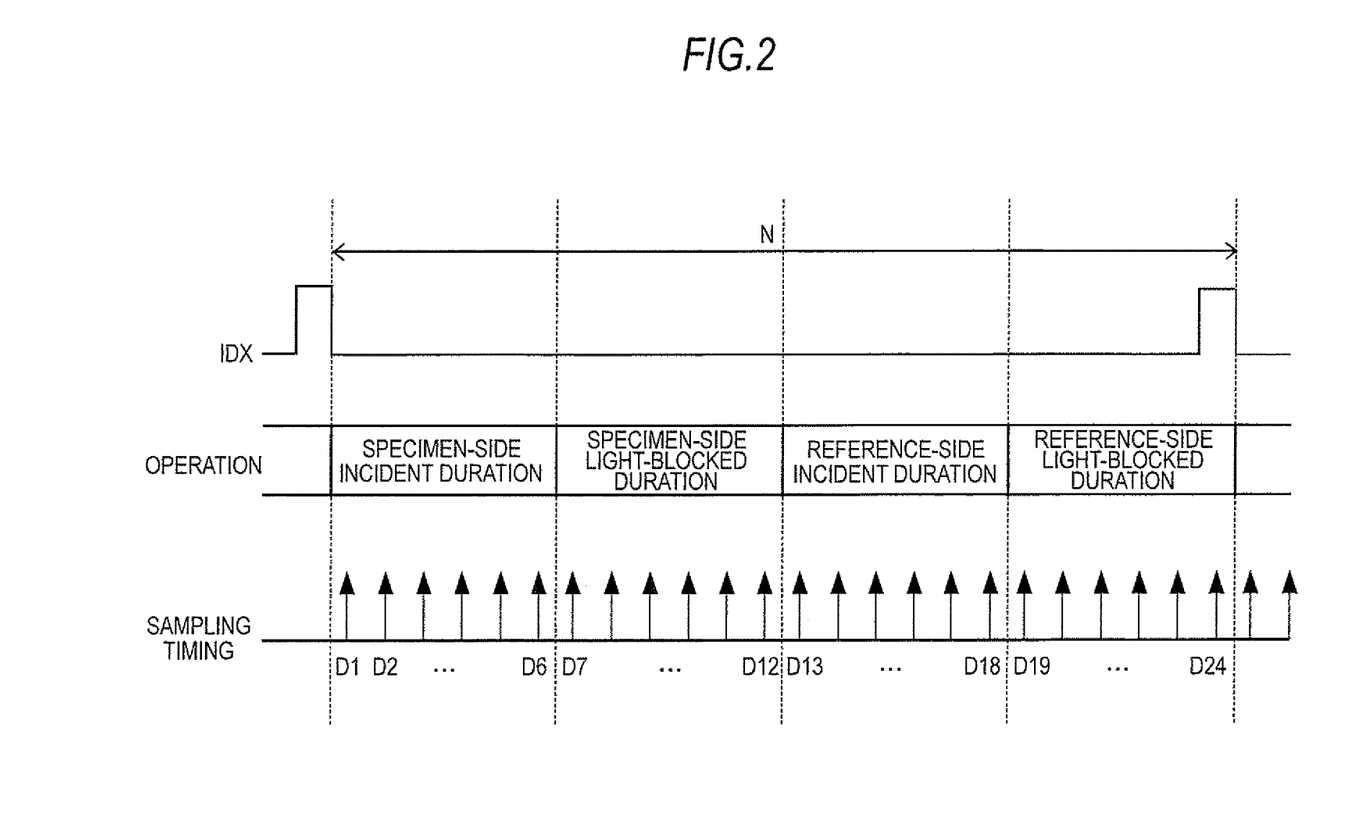
FIG. 2 shows a timing chart for one rotation period of a sector mirror.
Figure 3:
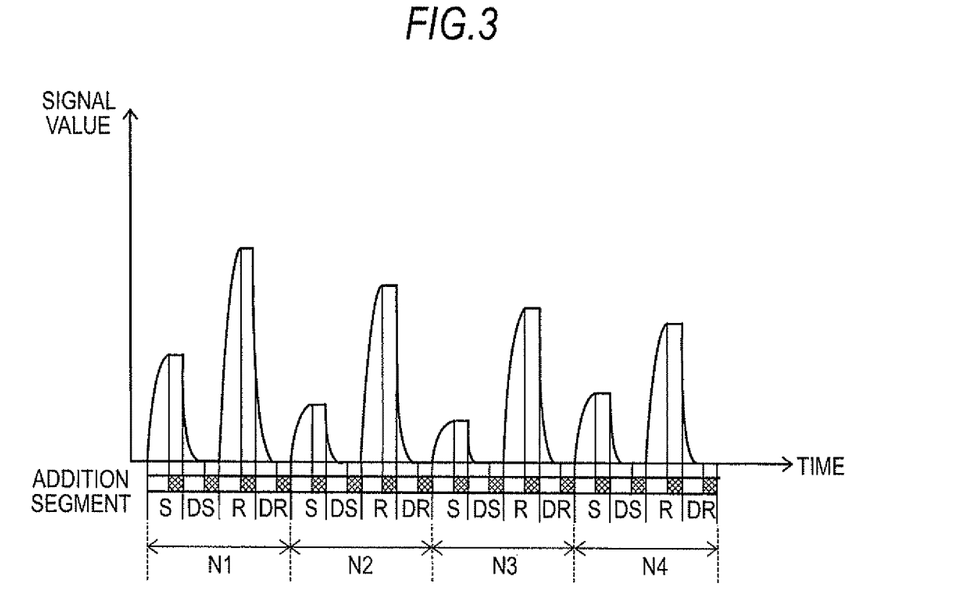
FIG. 3 is a chart showing one example of the relationship between time and signal value covering a plurality of periods.

FIG. 2 shows a timing chart for one rotation time span (which is defined as one period (N)) by sector mirror 40. FIG. 3 shows one example of the relationship between signal value (digital voltage value) and time for a plurality of periods.

During one period N, the photodetector outputs: output strength signal. S that corresponds to the incidence duration of specimen-side light beam LS; output strength signal DS that corresponds to the light-blocked duration of specimen-side light beam LS; output strength signal R that corresponds to the incidence duration of reference-side light beam LR; and output strength signal DR that corresponds to the light-blocked duration of reference-side light beam LR.

It should be noted that because the sampling period of A/D converter 14 is shorter than period N, a plurality (in this example, 6 each) of output data ("detection value data") is output from A/D converter 14 for each signal that is output during one period N. This means that D1 through D6, D7 through D12, D13 through D18, and D19 through D24 are each detection value data that correspond to output strength signal S, output strength signal DS, output strength signal R and output strength signal DR, respectively.

Computation controller 131b performs a control so that transmittance is calculated using the equation (19) below based on output strength signal S, output strength signal DS, output strength signal R and output strength signal DR, which are stored as afore-described in memory 134.

$$\text{Transmittance (\%)} = ((S_N - DS_N)/(R_N - DR_N))/Z \times 100 \quad (19)$$

Z is the value of $((S_N - DS_N)/(R_N - DR_N))$ stored in advance that was obtained by the measurement of a specimen (oftentimes water or air) used as control.

Specifically, for each period N, the average value for each of detection value data D4 through D6 corresponding to output strength signal SN, detection value data D10 through D12 corresponding to output strength signal DSN, detection value data D16 through D18 corresponding to output strength signal RN and detection value data D21 through D24 corresponding to output strength signal DRN is calculated. The average values are substituted into equation (19) to calculate the transmittance for the $N^{th}$ period.

PRIOR ART LITERATURE

Patent Literature

Patent Literature 1: Unexamined Patent Application Publication No. 2002-162294

OVERVIEW OF THE INVENTION

Problems to be Solved by the Invention

There has been a need in recent years for greater measurement accuracy in measuring specimens having a low transmittance. With the afore-described ultraviolet-visible spectrophotometer 160, there have been problems with measurement accuracy.

Means for Solving the Problems

This prompted the inventors of the present application to look for ways to solve the afore-described problems by improving the accuracy with which specimens having a low transmittance can be measured. With photodetector 12 such as a photomultiplier, detection value data representing output strength signals are successively sampled using a predetermined time interval. However, the effects of detection value data representing earlier output strength signal may remain. Hence, even in the absence of any incidence of light onto the light-receiving surface of photodetector 12, if the detection value data representing an earlier output strength signal shows a large light quantity, the detection value data of the output strength signal was not zero in some cases.

Because a plurality (with this example, 6) of detection value data (D1 through D6, D7 through D12, D13 through D18, D19 through D24) is obtained for each signal, what was done was to use only the detection value data (D4 through D6, D10 through D12, D16 through D18, D21 through D24) that was obtained during the latter half of time out of the plurality of detection value data. It is certainly conceivable to use only the detection value data (D5 through D6, D11 through D12, D17 through D18, D22 through D24) that is obtained during the latter half of time. However, even if that were done, the measurement accuracy could not be improved sufficiently because of the loss of S/N.

Figure 4:
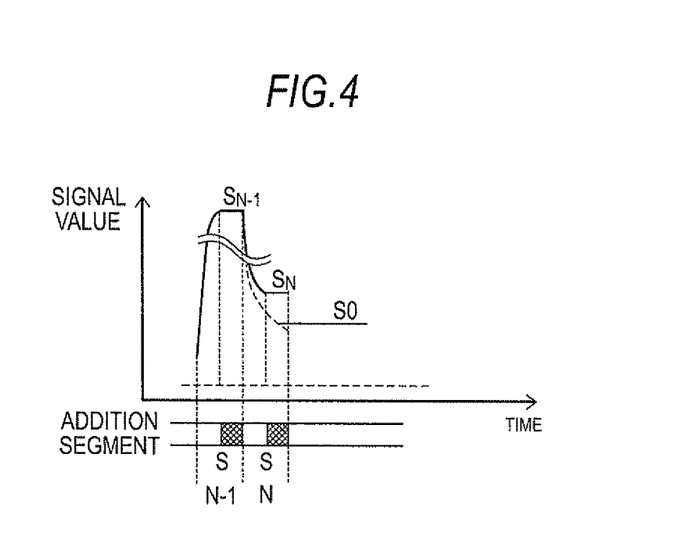
FIG. 4 is a chart showing one example of the relationship between time and signal value covering a plurality of periods.

This led to the creation of computation equations that eliminate the effects of earlier output strength signals that are included in output strength signals. In particular, since the effects are greatest from the immediately previous output strength signal, eliminating these effects is the most effective. The first to be studied was single-beam type ultraviolet-visible spectrophotometers. FIG. 4 is a chart showing one example of the relationship obtained from a single-beam type ultraviolet-visible spectrophotometer between time and signal value (digital voltage value) over a plurality of periods.

Referring to FIG. 4, even if the true output strength signal $s_N (=S_N - S0)$ is desired, it is not possible to measure S0 while measuring output strength signal $S_N$ for the incidence duration in the $N^{th}$ period. For this reason, S0 is estimated. Here, it is believed that S0 is not 0 due to the effects of output strength signal $S_{N-1}$ (i.e., the immediately previous output strength signal) from the incidence duration in the $(N-1)^{th}$ period. Therefore, based on experiments and calculations, the inventors computed the value of correction coefficient A for removing the effects of output strength signal $S_{N-1}$ from the incidence duration in the $(N-1)^{th}$ period that is included in output strength signal $S_N$ from the incidence duration in the $N^{th}$ period. This has led to the discovery of the use of correction coefficient A.

Figure 5:
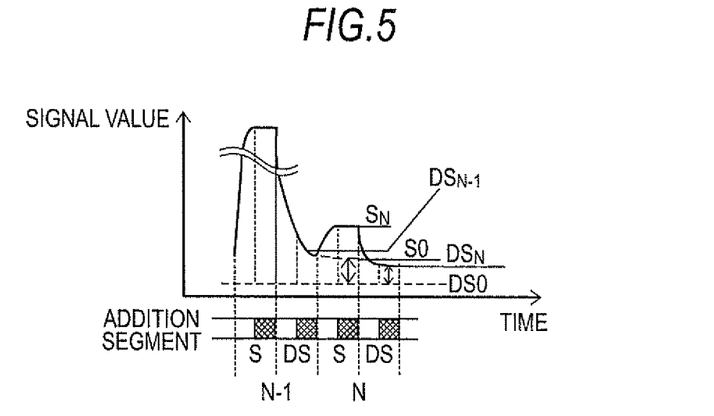
FIG. 5 is a chart showing one example of the relationship between time and signal value covering a plurality of periods.

FIG. 5 shows one example of the relationship between time and signal value (digital voltage value) over a plurality of periods obtained from a single-beam type ultraviolet-visible spectrophotometer having a light-shielding unit that prevents the incidence of measurement light onto a photodetector for a predetermined period so that the incidence duration and the light-blocked duration alternate. As afore-described, to eliminate the effects of output strength signal $S_{N-1}$ from the incidence duration of the $(N-1)^{th}$ period included in the output strength signal $S_N$ from the incidence duration in the $N^{th}$ period, correction coefficient B was determined through experiments and calculations. This led to the discovery of the use of correction coefficient B. Similarly, correction coefficient C for removing the effects of output strength signal $S_N$ from the incidence duration of the $N^{th}$ period included in output strength signal $DS_N$ of the light-blocked duration in the $N^{th}$ period was also determined through experiments and calculations. This led to the discovery of the use of correction coefficient C.

Also, if the output strength signal $S_N$ for the incidence duration of the $N^{th}$ period shows a small amount of light quantity and the output strength signal $S_{N-1}$ for the incidence duration in the $(N-1)^{th}$ period shows a large amount of light quantity (e.g., if the output strength signal $S_{N-1}$ shows a light quantity that is 100-fold or more greater than that of the output strength signal $S_N$), it is believed that the output strength signal $DS_{N-1}$ for the light-blocked duration of the $(N-1)^{th}$ period, the output strength signal $S_N$ of the incidence duration of the $N^{th}$ period, and the output strength signal $DS_N$ of the light-blocked duration of the $N^{th}$ period is primarily affected by the output strength signal $S_{N-1}$ of the incidence duration of the $(N-1)^{th}$ period. To explain, if the output strength signal $S_N$ for the incidence duration of the $N^{th}$ period shows a small light quantity and the output strength signal $S_{N-1}$ for the incidence duration of the $(N-1)^{th}$ period shows a large signal quantity, the effects of output strength signal $S_{N-1}$ of the incidence duration of $(N-1)^{th}$ period that is included in output strength signal $S_N$ of the incidence duration of the $N^{th}$ period are eliminated by using the output strength signal $DS_{N-1}$ of light-blocked duration of the $(N-1)^{th}$ period and the output strength signal $DS_N$ for the light-blocked duration of the $N^{th}$ period. These were used to experimentally or computationally calculate the value of correction coefficient D that is used for eliminating the effects of output strength signal $S_{N-1}$ of the incidence duration of the $(N-1)^{th}$ period. This led to the discovery of the use of correction coefficient D.

Figure 6:
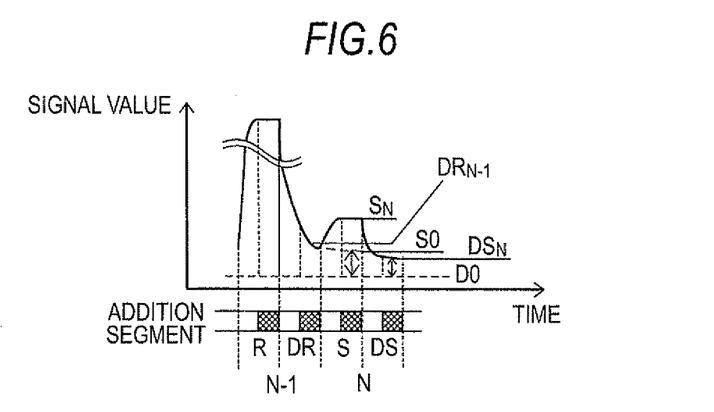
FIG. 6 is a chart showing one example of the relationship between time and signal value covering a plurality of periods.
Figure 7:
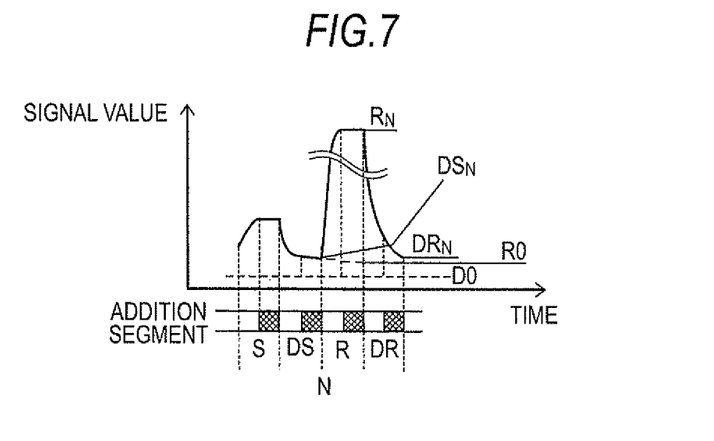
FIG. 7 is a chart showing one example of the relationship between time and signal value covering a plurality of periods.

Next, studies were made into double-beam type ultraviolet-visible spectrophotometers. FIG. 6 and FIG. 7 show examples of the relationship between time and signal values (digital voltage values) that were obtained by a double-beam type ultraviolet-visible spectrophotometer over a plurality of periods. Just as with a single-beam type ultraviolet-visible spectrophotometer, the inventors discovered the use of correction coefficients E, F, G and H.

To explain, the spectrophotometer according to the present invention includes: a specimen cell; a light source unit for emitting measurement light to the specimen cell; a photodetector for detecting light that has passed through the specimen cell; a memory unit for storing output strength signals obtained by the photodetector; and a controller for calculating transmittance or absorbance based on output strength signal S that is stored in the memory unit. The controller calculates the true output strength signal $s_N$ for the incidence duration of the $N^{th}$ period that is removed of the effects of output strength signals $S_{N-1}, S_{N-2}, S_{N-3}, \ldots$ of the incidence duration belonging to the $(N-1)^{th}$ period and earlier, which are included in the output strength signal $s_N$ for the incidence duration of the $N^{th}$ period.

Examples of a "photodetector" referred to here include photomultipliers, PbS photoconductive devices, photodiodes and the like.

Effects of the Invention

As afore-described, with a spectrophotometer according to the present invention, the measurement accuracy is improved by the elimination of the effects of output strength signals $S_{N-1}, S_{N-2}, S_{N-3}, \ldots$ of the incidence durations in the $(N-1)^{th}$ period and earlier that are included in output strength signal $S_N$ of the incidence duration of the $N^{th}$ period.

Other Means for Solving the Problems, and Effects

Furthermore, with the afore-described invention, it is possible for the aforesaid memory unit to store correction coefficient A for eliminating the effects of output strength signal $S_{N-1}$ of the incidence duration in the $(N-1)^{th}$ period that are included in output strength signal $S_N$ of the incidence duration of the $N^{th}$ period and for the aforesaid controller to use equation (1) below to calculate the true output strength signal $s_N$ for the $N^{th}$ period.

$$s_N = (S_N - S_{N-1} \times A) \tag{1}$$

Here, the term "correction coefficient A" refers to a numerical value or an equation that is determined in advance either experimentally or computationally for each detector or wavelength λ for eliminating the effects of output strength signal $S_{N-1}$ of the incidence duration in the $(N-1)^{th}$ period that are included in output strength signal $S_N$ of the incidence duration of the $N^{th}$ period. For example, for each wavelength λ, the correction coefficient A can be determined experimentally by measuring multiple times the change in output strength signal after the incidence of light to a photodetector and obtaining an average.

The spectrophotometer according to the present invention further comprises a light-shielding unit for preventing the incidence of measurement light from the light source unit onto the photodetector for predetermined periods so that an incidence duration and light-blocked duration occur in this sequence in a single period; wherein: the memory unit stores the output strength signal obtained by the photodetector in association with the light-blocked duration when light is blocked by the light-shielding unit; and the controller calculates transmittance or absorbance based on output strength signal (S) of the incidence duration and output strength signal (DS) of the light-blocked duration that are stored in the memory unit.

Furthermore, in the aforesaid invention, it is acceptable for the aforesaid memory unit to store correction coefficient B for eliminating the effects of output strength signal $S_{N-1}$ of the incidence duration in the $(N-1)^{th}$ period that are included in output strength signal $S_N$ of the incidence duration of the $N^{th}$ period and for the aforesaid controller to use equation (2) below to calculate the true output strength signal $s_N$ for the $N^{th}$ period.

$$s_N = (S_N - S_{N-1} \times B) - DS_N \tag{2}$$

Here, in consideration of the existence of the light-blocking duration, the "correction coefficient B" is a numerical value or an equation that is determined in advance either experimentally or computationally for each detector or wavelength λ for eliminating the effects of output strength signal $S_{N-1}$ of the incidence duration of the $(N-1)^{th}$ period that are included in output strength signal $S_N$ of the incidence duration of the $N^{th}$ period. For example, for each wavelength λ, the correction coefficient B can be determined experimentally by measuring multiple times the change in output strength signal after the incidence of light to a photodetector and obtaining an average.

Furthermore, in the aforesaid invention, it is acceptable for the aforesaid memory unit to store correction coefficient B for eliminating the effects of output strength signal $S_{N-1}$ of the incidence duration in the $(N-1)^{th}$ period that are included in output strength signal $S_N$ of the incidence duration of the $N^{th}$ period and to store correction coefficient C for eliminating the effects of output strength signal $S_N$ of the incidence duration in the $N^{th}$ period that are included in output strength signal $DS_N$ of the light-blocked duration of the $N^{th}$ period and for the aforesaid controller to use equation (3) below to calculate the true output strength signal $s_N$ for the $N^{th}$ period.

$$s_N = (S_N - S_{N-1} \times B) - (DS_N - S_N \times C) \tag{3}$$

Here, the term "correction coefficient C" refers to a numerical value or an equation that is determined in advance either experimentally or computationally for each detector or wavelength λ for eliminating the effects of output strength signal $S_N$ of the incidence duration in the $N^{th}$ period that are included in output strength signal $DS_N$ of the light-blocked duration of the $N^{th}$ period. For example, for each wavelength λ, the correction coefficient C can be determined experimentally by measuring multiple times the change in output strength signal after the incidence of light to a photodetector and obtaining an average.

Furthermore, in the aforesaid invention, it is acceptable for the aforesaid memory unit to store correction coefficient D for eliminating the effects of output strength signal $S_{N-1}$ of the incidence duration in the $(N-1)^{th}$ period that are included in output strength signal $S_N$ of the incidence duration of the $N^{th}$ period and for the aforesaid controller to use equation (4) below to calculate the true output strength signal $s_N$ for the $N^{th}$ period.

$$s_N = S_N - (DS_{N-1} - DS_N) \times \tfrac{1}{2} \times D - DS_N \tag{4}$$

Here, the term "correction coefficient D" refers to a numerical value or an equation that is determined in advance either experimentally or computationally for each detector or wavelength λ for eliminating the effects of output strength signal $S_{N-1}$ of the incidence duration in the $(N-1)^{th}$ period that are included in output strength signal $S_N$ of the incidence duration of the $N^{th}$ period in the event that the output strength signal $S_N$ of the incidence duration of the $N^{th}$ period shows a low light quantity while the output strength signal $S_{N-1}$ of the incidence duration of the $(N-1)^{th}$ period shows a large light quantity (e.g., when the output strength signal $S_{N-1}$ shows a light quantity that is 100-fold or more of that of the output strength signal $S_N$). For example, for each wavelength λ, the correction coefficient D can be determined experimentally by measuring multiple times the change in output strength signal after the incidence of light to a photodetector and obtaining an average. If $S_N$ indicates a light quantity that is greater than that shown by $S_{N-1}$, the correction amount $((DS_{N-1}-DS_N) \times \frac{1}{2} \times D)$ that is calculated will be smaller than $S_N$ and can be ignored, allowing the above correction to be used as is.

The afore-described invention further comprises: a reference cell; a second photodetector for detecting the measurement light that has passed through the reference cell; and a splitter for splitting the measurement light to the specimen cell and the reference cell; wherein: the memory unit stores the output strength signal obtained by the second photodetector; the controller calculates transmittance or absorbance based on specimen-side output strength signal S and reference-side output strength signal R that are stored in the memory unit; and the controller calculates true reference-side output strength signal $r_N$ of the $N^{th}$ period that is removed of the effects of the output strength signals $R_{N-1}, R_{N-2}, R_{N-3}, \ldots$ of the reference-side incidence duration of the $(N-1)^{th}$ period and earlier included in the output strength signal $R_N$ of the reference-side incidence duration of the $N^{th}$ period.

Furthermore, in the aforesaid invention, it is acceptable for the aforesaid memory unit to store correction coefficient E for eliminating the effects of output strength signal $S_{N-1}$ of the specimen-side incidence duration in the $(N-1)^{th}$ period that are included in output strength signal $S_N$ of the specimen-side incidence duration of the $N^{th}$ period and to store correction coefficient E' for eliminating the effects of output strength signal $R_{N-1}$ of the reference-side incidence duration in the $(N-1)^{th}$ period that are included in output strength signal $R_N$ of the reference-side incidence duration of the $N^{th}$ period and for the aforesaid controller to use equation (5) below to calculate the true output strength signal $s_N$ for the $N^{th}$ period and to use equation (6) below to calculate true reference-side output strength signal $r_N$ of the $N^{th}$ period.

$$s_N = (S_N - S_{N-1} \times E) \quad (5)$$

$$r_N = (R_N - R_{N-1} \times E') \quad (6)$$

Here, the term "correction coefficient E" refers to a numerical value or an equation that is determined in advance either experimentally or computationally for each detector or wavelength λ for eliminating the effects of output strength signal $S_{N-1}$ of the specimen-side incidence duration in the $(N-1)^{th}$ period that are included in output strength signal $S_N$ of the specimen-side incidence duration of the $N^{th}$ period. For example, for each wavelength λ, the correction coefficient E can be determined experimentally by measuring multiple times the change in output strength signal after the incidence of light to a photodetector and obtaining an average.

The term "correction coefficient E'" refers to a numerical value or an equation that is determined in advance either experimentally or computationally for each detector or wavelength λ for eliminating the effects of output strength signal $R_{N-1}$ of the reference-side incidence duration in the $(N-1)^{th}$ period that are included in output strength signal $R_N$ of the reference-side incidence duration of the $N^{th}$ period. For example, for each wavelength λ, the correction coefficient E' can be determined experimentally by measuring multiple times the change in output strength signal after the incidence of light to a photodetector and obtaining an average. The correction coefficient E' can be the same as correction coefficient E.

Furthermore, the spectrophotometer according to the present invention comprises: a specimen cell; a light source unit for emitting measurement light to the specimen cell; a photodetector for detecting the measurement light that has passed through the specimen cell; a light-shielding unit for preventing the incidence of the measurement light from the light source unit to the photodetector at predetermined periods; a reference cell; a switching unit for switchably guiding the measurement light to the reference cell instead of the specimen cell at predetermined periods; a memory unit for storing the output strength signals detected by the photodetector in association with a light-blocked duration when light is blocked by the light-shielding unit and switched duration when the optical path is switched by the switching unit; and a controller for calculating transmittance or absorbance based on output strength signal S of the specimen-side incidence duration, output strength signal DS of the specimen-side light-blocked duration, output strength signal R of the reference-side incidence duration and output strength signal DR of the reference-side light-blocked duration that are stored in the memory unit; wherein: the specimen-side incidence duration, specimen-side light-blocked duration, reference-side incidence duration and reference-side light-blocked duration occur in this sequence in a single period; and the controller calculates the true specimen-side output strength signal $s_N$ of the $N^{th}$ period removed of the effects of output strength signal $R_{N-1}, S_{N-1}, R_{N-2}, S_{N-2}, \ldots$ prior to the reference-side incidence duration of the $(N-1)^{th}$ period that are included in the output strength signal $S_N$ of the specimen-side incidence duration of the $N^{th}$ period and calculates the true reference-side output strength signal $r_N$ of the $N^{th}$ period removed of the effects of output strength signal $S_N, R_{N-1}, S_{N-1}, R_{N-2}, \ldots$ prior to the specimen-side incidence duration of the $N^{th}$ period that are included in the output strength signal $R_N$ of the reference-side incidence duration of the $N^{th}$ period.

Furthermore, with the spectrophotometer according to the aforesaid invention, since the effects of output strength signals $R_{N-1}, S_{N-1}, R_{N-2}, S_{N-2}, \ldots$ in the reference-side incidence duration in and before the $(N-1)^{th}$ period included in output strength signal $S_N$ of the specimen-side incidence duration of the $N^{th}$ period are eliminated, and moreover, since the effects of output strength signals $S_N, R_{N-1}, S_{N-1}, R_{N-2}, \ldots$ in the specimen-side incidence duration in and before the $N^{th}$ period included in output strength signal $R_N$ of the reference-side incidence duration of the $N^{th}$ period are eliminated, the measurement accuracy is improved.

Furthermore, in the aforesaid invention, it is acceptable for the aforesaid memory unit to store correction coefficient F for eliminating the effects of output strength signal $R_{N-1}$ of the reference-side incidence duration in the $(N-1)^{th}$ period that are included in output strength signal $S_N$ of the specimen-side incidence duration of the $N^{th}$ period and to store correction coefficient F' for eliminating the effects of output strength signal $R_N$ of the reference-side incidence duration in the $N^{th}$ period that are included in output strength signal $R_N$ of the reference-side incidence duration of the $N^{th}$ period and for the aforesaid controller to use equation (7) below to calculate the true specimen-side output strength signal $s_N$ for the $N^{th}$ period and to use equation (8) below to calculate true reference-side output strength signal $r_N$ of the $N^{th}$ period.

$$s_N = (S_N - R_{N-1} \times F) - DS_N \quad (7)$$

$$r_N = (R_N - S_N \times F') - DR_N \quad (8)$$

Here, in consideration of the existence of the light-blocking duration, the "correction coefficient F" is a numerical value or an equation that is determined in advance either experimentally or computationally for each detector or wavelength λ for eliminating the effects of output strength signal $R_{N-1}$ of the reference-side incidence duration of the $(N-1)^{th}$ period that are included in output strength signal $S_N$ of the specimen-side incidence duration of the $N^{th}$ period. For example, for each wavelength λ, the correction coefficient F can be determined experimentally by measuring multiple times the change in output strength signal after the incidence of light to a photodetector and obtaining an average.

Also, in consideration of the existence of the light-blocking duration, the "correction coefficient F'" is a numerical value or an equation that is determined in advance either experimentally or computationally for each detector or wavelength λ for eliminating the effects of output strength signal $S_N$ of the specimen-side incidence duration of the $N^{th}$ period that are included in output strength signal $R_N$ of the reference-side incidence duration of the $N^{th}$ period. For example, for each wavelength λ, the correction coefficient F' can be determined experimentally by measuring multiple times the change in output strength signal after the incidence of light to a photodetector and obtaining an average. The correction coefficient F' can be the same as correction coefficient F.

Furthermore, in the aforesaid invention, it is acceptable for the aforesaid memory unit to store correction coefficient F for eliminating the effects of output strength signal $R_{N-1}$ of the reference-side incidence duration in the $(N-1)^{th}$ period that are included in output strength signal $S_N$ of the specimen-side incidence duration of the $N^{th}$ period and to store correction coefficient F' for eliminating the effects of output strength signal $S_N$ of the specimen-side incidence duration in the $N^{th}$ period that are included in output strength signal $R_N$ of the reference-side incidence duration of the $N^{th}$ period and to store correction coefficient G for eliminating the effects of output strength signal $S_N$ of the specimen-side incidence duration in the $N^{th}$ period that are included in output strength signal $DS_N$ of the specimen-side light-blocked duration of the $N^{th}$ period and to store correction coefficient G' for eliminating the effects of output strength signal $R_N$ of the reference-side incidence duration in the $N^{th}$ period that are included in output strength signal $DR_N$ of the reference-side light-blocked duration of the $N^{th}$ period and for the aforesaid controller to use equation (9) below to calculate the true specimen-side output strength signal $s_N$ for the $N^{th}$ period and to use equation (10) below to calculate true reference-side output strength signal $r_N$ of the $N^{th}$ period.

$$s_N = (S_N - R_{N-1} \times F) - (DS_N - S_N \times G) \tag{9}$$

$$r_N = (R_N - S_N \times F') - (DR_N - R_N \times G') \tag{10}$$

Here, the "correction coefficient G" is a numerical value or an equation that is determined in advance either experimentally or computationally for each detector or wavelength λ for eliminating the effects of output strength signal $S_N$ of the incidence duration of the $N^{th}$ period that are included in output strength signal $DS_N$ of the specimen-side light-blocked duration of the $N^{th}$ period. For example, for each wavelength λ, the correction coefficient G can be determined experimentally by measuring multiple times the change in output strength signal after the incidence of light to a photodetector and obtaining an average.

Also, the "correction coefficient G'" is a numerical value or an equation that is determined in advance either experimentally or computationally for each detector or wavelength λ for eliminating the effects of output strength signal $R_N$ of the reference-side incidence duration of the $N^{th}$ period that are included in output strength signal $DR_N$ of the reference-side light-blocked duration of the $N^{th}$ period. For example, for each wavelength λ, the correction coefficient G' can be determined experimentally by measuring multiple times the change in output strength signal after the incidence of light to a photodetector and obtaining an average. The correction coefficient G' can be the same as correction coefficient G.

Furthermore, in the aforesaid invention, it is acceptable for the aforesaid memory unit to store correction coefficient H for eliminating the effects of output strength signal $R_{N-1}$ of the reference-side incidence duration in the $(N-1)^{th}$ period that are included in output strength signal $S_N$ of the specimen-side incidence duration of the $N^{th}$ period and to store correction coefficient if for eliminating the effects of output strength signal $S_N$ of the specimen-side incidence duration in the $N^{th}$ period that are included in output strength signal $R_N$ of the reference-side incidence duration of the $N^{th}$ period and for the aforesaid controller to use equation (11) below to calculate the true specimen-side output strength signal $s_N$ for the $N^{th}$ period and to use equation (12) below to calculate true reference-side output strength signal $r_N$ of the $N^{th}$ period.

$$s_N = S_N - (DR_{N-1} - DS_N) \times \tfrac{1}{2} \times H - DS_N \tag{11}$$

$$r_N = R_N - (DS_N - DR_N) \times \tfrac{1}{2} \times H' - DR_N \tag{12}$$

Here, the "correction coefficient H" is a numerical value or an equation that is determined in advance either experimentally or computationally for each detector or wavelength λ for eliminating the effects of output strength signal $R_{N-1}$ of the reference-side incidence duration of the $(N-1)^{th}$ period that are included in output strength signal $S_N$ of the specimen-side incidence duration of the $N^{th}$ period in case the output strength signal $S_N$ of the incidence duration of the $N^{th}$ period shows a small light quantity and the output strength signal $R_{N-1}$ of the reference-side incidence duration of the $(N-1)^{th}$ period shows a large light quantity (e.g., when the light quantity identified by the output strength signal $R_{N-1}$ is 100-fold or more greater than that identified by the output strength signal $S_N$). For example, for each wavelength λ, the correction coefficient H can be determined experimentally by measuring multiple times the change in output strength signal after the incidence of light to a photodetector and obtaining an average. If SN indicates a light quantity that is greater than that shown by $R_{N-1}$, the correction amount $((DR_{N-1} - DS_N) \times \tfrac{1}{2} \times H)$ that is calculated will be smaller than $S_N$ and can be ignored, allowing the above correction to be used as is.

Also, the "correction coefficient H'" is a numerical value or an equation that is determined in advance either experimentally or computationally for each detector or wavelength λ for eliminating the effects of output strength signal $S_N$ of the specimen-side incidence duration of the $N^{th}$ period that are included in output strength signal $R_N$ of the reference-side incidence duration of the $N^{th}$ period in case the output strength signal $R_N$ of the reference-side incidence duration of the $N^{th}$ period shows a small light quantity and the output strength signal $S_N$ of the specimen-side incidence duration of the $N^{th}$ period shows a large light quantity (e.g., when the light quantity identified by the output strength signal $S_N$ is 100-fold or more greater than that identified by the output strength signal $R_N$). For example, for each wavelength λ, the correction coefficient H' can be determined experimentally by measuring multiple times the change in output strength signal after the incidence of light to a photodetector and obtaining an average. The correction coefficient H' may be the same as correction coefficient H. If $R_N$ indicates a light quantity that is greater than that shown by $S_N$, the correction amount ($(DS_N -$ $DR_N) \times \frac{1}{2} \times H')$ that is calculated will be smaller than $R_N$ and can be ignored, allowing the above correction to be used as is.

BRIEF DESCRIPTION OF THE FIGURES

FIG. 8 shows a schematic view of the configuration of a single-beam type ultraviolet-visible spectrophotometer as a second embodiment of the present invention as.

MODES FOR PRACTICING THE INVENTION

Embodiments of the present invention are described next with reference to figures. The present invention is not limited to the embodiments described below, and needless to say, various other modes of the invention are possible without deviating from the gist of the present invention.

First Embodiment

Figure 1:
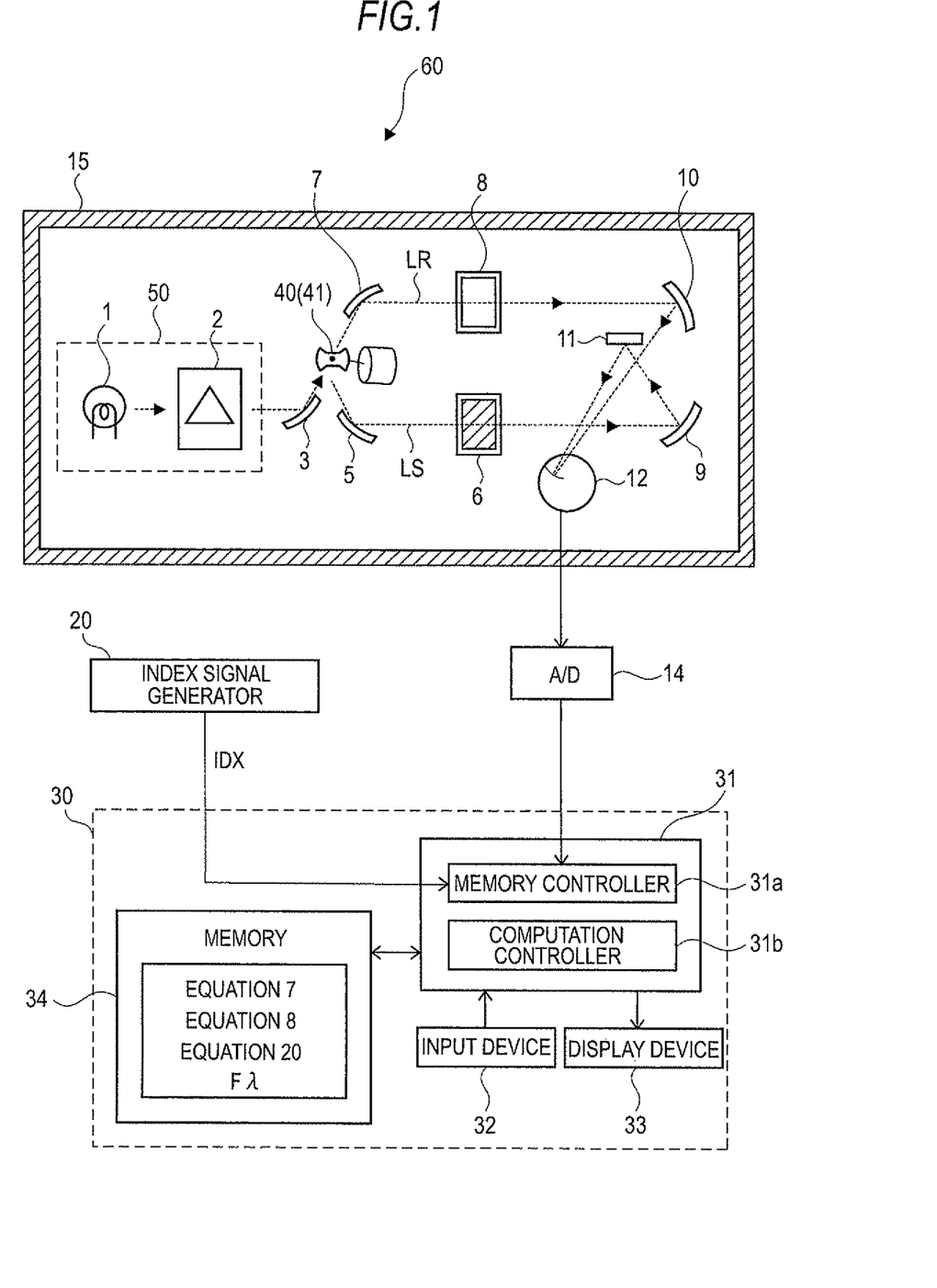
FIG. 1 shows a schematic view of the configuration of a double-beam type ultraviolet-visible spectrophotometer as a first embodiment of the present invention.

FIG. 1 shows a schematic view of the configuration of a first embodiment of the present invention as a double-beam type ultraviolet-visible spectrophotometer. The same numerical references are used for the same components as in ultraviolet-visible spectrophotometer 160.

The ultraviolet-visible spectrophotometer 60 comprises: a specimen cell 6; a reference cell 8; a light source unit 50 comprising a spectrometer 2 and a light source 1 for emitting a measurement light; photodetector 12; a sector mirror (switching unit and light-shielding unit) 40; a plurality of reflecting mirrors 3, 5, 7, 9, 10 and 11; an enclosure 15 that does not allow light to pass through; an index signal generator 20; an analog/digital (A/D) converter 14; and a computer 30 that controls the overall ultraviolet-visible spectrophotometer 60.

The computer 30 comprises a CPU (controller) 31 and a memory (memory unit) 34 and is further connected to a display device 33 and an input device 32 comprising a keyboard, mouse and the like. To explain the functional blocks of the CPU 31, CPU 31 comprises a memory controller 31a for storing in memory 34 the output strength signal from a photodetector 12 and a computation controller 31b for calculating transmittance.

Here, equation (7), equation (8), equation (20) and correction coefficient $F\lambda$, ($F\lambda 1$, $F\lambda 2$, $F\lambda 3$, . . . ) are stored in advance in memory 34.

$$s_N = (S_N - R_{N-1} \times F\lambda) - DS_N \quad (7)$$

$$r_N = (R_N - S_N \times F\lambda) - DR_N \quad (8)$$

$$\text{Transmittance } (\%) = (s_N/r_N)/Z \times 100 \quad (20)$$

Z is the value of $(s_N/r_N)$ stored in advance that was obtained by the measurement of a specimen (oftentimes water or air) used as control.

The correction coefficient $F\lambda$, is a numerical value that is determined in advance either experimentally or computationally for each wavelength $\lambda 1$, $\lambda 2$, $\lambda 3$, . . . for eliminating the effects of output strength signal $S_N$ of specimen-side incidence duration of the $N^{th}$ period included in output strength signal $R_N$ of the reference-side incidence duration of the $N^{th}$ period or eliminating the effects of output strength signal $R_{N-1}$ of the reference-side incidence duration of the $(N-1)^{th}$ period included in output strength signal $S_N$ of the specimen-side incidence duration of the $N^{th}$ period. For example, for each wavelength $\lambda 1$, $\lambda 2$, $\lambda 3$, . . . , the correction coefficient $F\lambda$ can be determined experimentally by measuring multiple times the change in output strength signal after the incidence of light to photodetector 12 and obtaining an average.

Furthermore, equation (7) may be equation (7'). Ordinarily, measurements under the same conditions are repeated over a plurality of periods, and even if the period N were to advance forward, dramatic changes in light quantity are rare, and ordinarily $R_{N-1} = R_N$.

$$s_N = (S_N - R_N \times F\lambda) - DS_N \quad (7')$$

Computation controller 31b performs the control that uses equation (7), equation (8), equation (20) and correction coefficients $F\lambda 1$, $F\lambda 2$, $F\lambda 3$, . . . to calculate transmittance.

Specifically, wavelength $\lambda$ of the measurement light that was extracted by spectrometer 2 is acquired, and the average value of detection value data D16 through D18 corresponding to output strength signal $R_{N-1}$ in the $(N-1)^{th}$ period is calculated. Furthermore, in the $N^{th}$ period, the average values are calculated for detection value data D4 through D6 corresponding to output strength signal $S_N$, detection value data D10 through D12 corresponding to output strength signal $DS_N$, detection value data D16 through D18 corresponding to output strength signal $R_N$, and detection value data D21 through D24 corresponding to output strength signal $DR_N$. The average values are substituted into equation (7) and equation (8) and the true specimen-side output strength signal $s_N$ and true reference-side output strength signal $r_N$ are determined for the $N^{th}$ period. The true specimen-side output strength signal $s_N$ and true reference-side output strength signal $r_N$ for the $N^{th}$ period are substituted into equation (20) to determine the transmittance for the $N^{th}$ period. Furthermore, the average value of detection value data D16 through D18 for the $N^{th}$ period corresponding to output strength signal $R_N$ is calculated. Furthermore, in the $(N+1)^{th}$ period, the average values are calculated for detection value data D4 through D6 corresponding to output strength signal $S_{N+1}$, detection value data D10 through D12 corresponding to output strength signal $DS_{N+1}$, detection value data D16 through D18 corresponding to output strength signal $R_{N+1}$, and detection value data D21 through D24 corresponding to output strength signal $DR_{N+1}$. The average values are substituted into equation (7) and equation (8) and the true specimen-side output strength signal $s_N$ and true reference-side output strength signal $r_N$ are determined for the $(N+1)^{th}$ period. The true specimen-side output strength signal $s_N$ and true reference-side output strength signal $r_N$ for the $(N+1)^{th}$ period are substituted into equation (20) to determine the transmittance for the $(N+1)^{th}$ period. In this way, the transmittance of the $N^{th}$ period is successively determined.

In the foregoing way, ultraviolet-visible spectrophotometer 60 eliminates the effects of output strength signal $R_{N-1}$ of the reference-side incidence duration of the $(N-1)^{th}$ period that are included in the output strength signal $S_N$ of the specimen-side incidence duration of the $N^{th}$ period and also eliminates the effects of output strength signal $S_N$ of specimen-side incidence duration of the $N^{th}$ period that is included in output strength signal $R_N$ of the reference-side incidence duration of the $N^{th}$ period, thereby improving the measurement accuracy.

Second Embodiment

Figure 8:
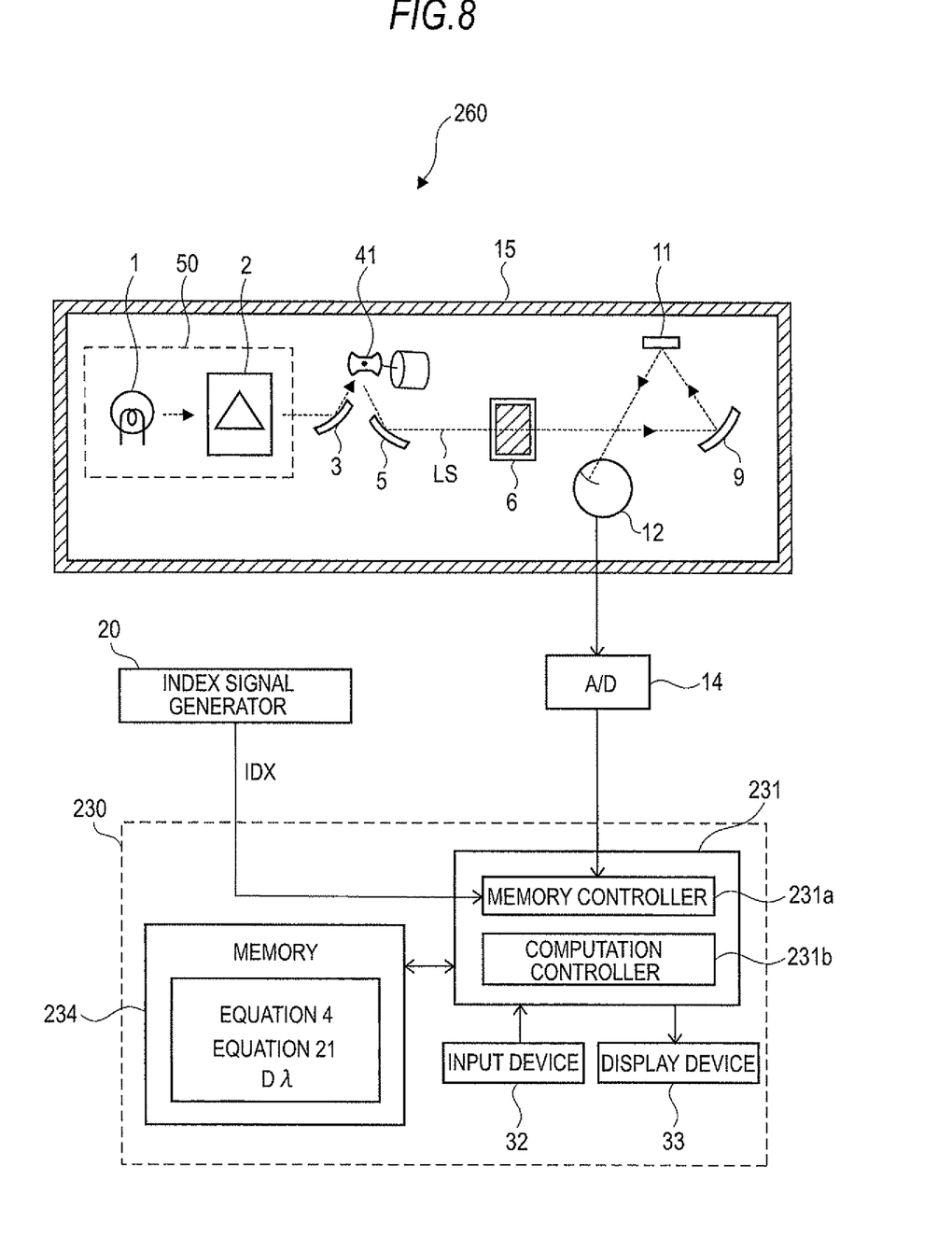

FIG. 8 shows a schematic view of the configuration of a second embodiment of the present invention as a single-beam type ultraviolet-visible spectrophotometer. The same numerical references are used for the same components as in ultraviolet-visible spectrophotometer 160.

The ultraviolet-visible spectrophotometer 260 comprises: a specimen cell 6; a light source unit 50 comprising a spectrometer 2 and a light source 1 for emitting measurement light; photodetector 12; a light-shielding unit 41; a plurality of reflecting mirrors 3, 5, 9 and 11; an enclosure 15 that does not allow light to pass through; an index signal generator 20; an analog/digital (A/D) converter 14; and a computer 230 that controls the overall ultraviolet-visible spectrophotometer 260.

The computer 230 comprises a CPU (controller) 231 and a memory (memory unit) 234 and is further connected to a display device 33 and an input device 32 comprising a keyboard, mouse and the like. To explain the functional blocks of the CPU 231, CPU 231 comprises a memory controller 231a for storing in memory 234 the output strength signal from a photodetector 12 and a computation controller 231b for calculating transmittance.

Here, equation (4) and equation (21) and correction coefficients $D\lambda$ ($D\lambda 1$, $D\lambda 2$, $D\lambda 3$, . . . ) are stored in advance in memory 234.

$$s_N = S_N - (DS_{N-1} - DS_N) \times \tfrac{1}{2} \times D\lambda - DS_N \qquad (4)$$

$$\text{Transmittance (\%)} = s_N/Z \times 100 \qquad (21)$$

Z is the value of $s_N$ stored in advance that was obtained by the measurement of a specimen (oftentimes water or air) used as control.

The correction coefficient $D\lambda$ is a numerical value that is determined in advance either experimentally or computationally for each wavelength $\lambda 1$, $\lambda 2$, $\lambda 3$, . . . for eliminating the effects of output strength signal $S_{N-1}$ of incidence duration of the $(N-1)^{th}$ period included in output strength signal $S_N$ of the incidence duration of the $N^{th}$ period. For example, for each wavelength $\lambda 1$, $\lambda 2$, $\lambda 3$, . . . , the correction coefficient $D\lambda$ can be determined experimentally by measuring multiple times the change in output strength signal after the incidence of light to photodetector 12 and obtaining an average.

Computation controller 231b performs the control that uses equation (4) and equation (21) and correction coefficients $D\lambda 1$, $D\lambda 2$, $D\lambda 3$, . . . to calculate transmittance.

Specifically, wavelength $\lambda$ of the measurement light that was extracted by spectrometer 2 is acquired, and the average value of detection value data corresponding to output strength signal $DS_{N-1}$ in the $(N-1)^{th}$ period is calculated. Furthermore, in the $N^{th}$ period, the average values are calculated for detection value data corresponding to output strength signal $S_N$ and detection value data corresponding to output strength signal $DS_N$. The average values are substituted into equation (4), and the true specimen-side output strength signal $s_N$ is determined for the $N^{th}$ period. Then, the true specimen-side output strength signal $s_N$ for the $N^{th}$ period is substituted into equation (21) to determine the transmittance for the $N^{th}$ period. In this way, the transmittance for the $N^{th}$ period is successively determined.

In the foregoing way, ultraviolet-visible spectrophotometer 260 eliminates the effects of output strength signal $S_{N-1}$ of the incidence duration of the $(N-1)^{th}$ period that are included in the output strength signal $S_N$ of the incidence duration of the $N^{th}$ period, thereby improving the measurement accuracy.

Third Embodiment

Figure 9:
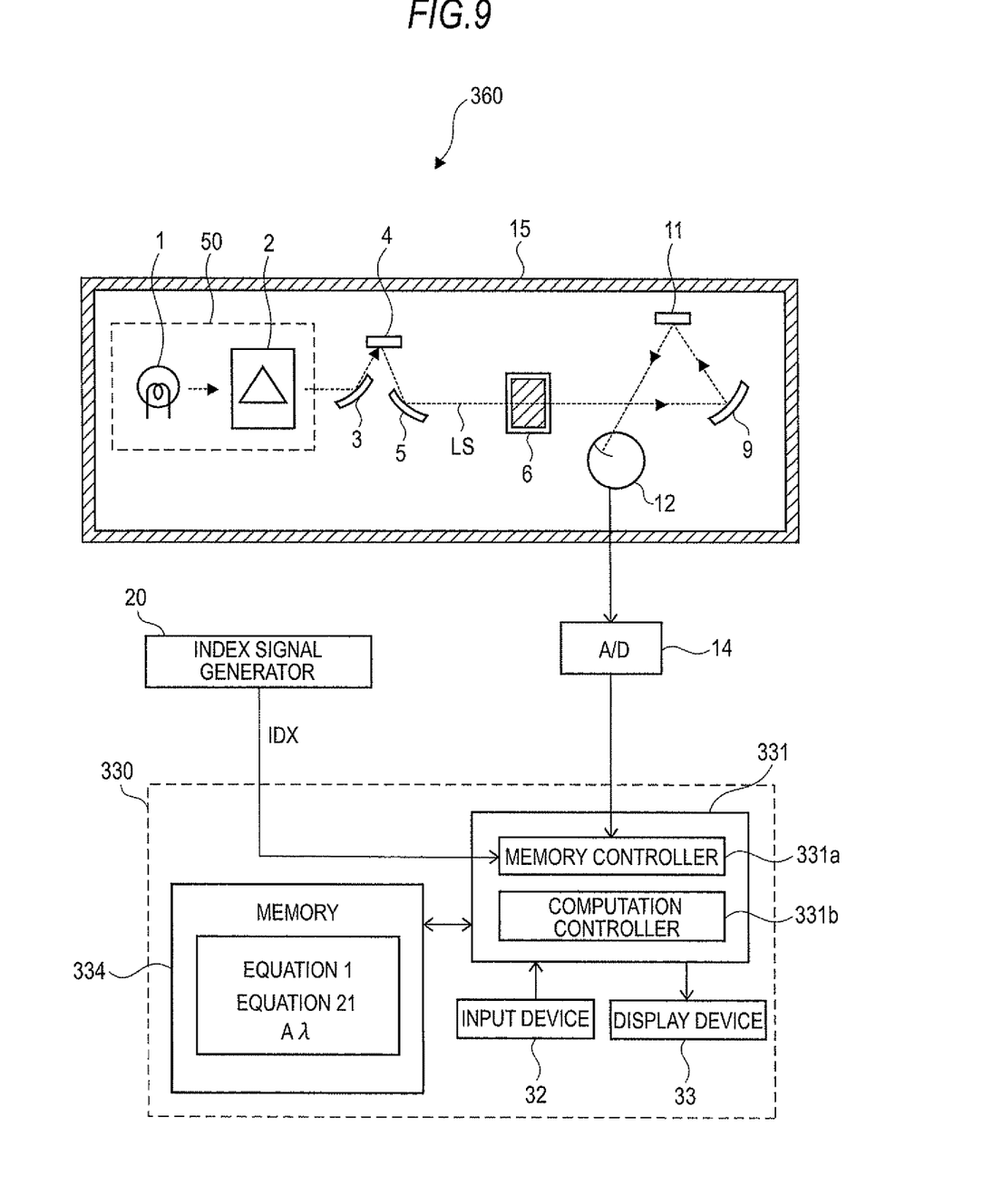
FIG. 9 shows a schematic view of the configuration of a single-beam type ultraviolet-visible spectrophotometer as a third embodiment of the present invention.

FIG. 9 shows a schematic view of the configuration of a third embodiment of the present invention as a single-beam type ultraviolet-visible spectrophotometer that does not have predetermined alternating periods of incidence duration and light-blocked duration. The same numerical references are used for the same components as in ultraviolet-visible spectrophotometer 160.

The ultraviolet-visible spectrophotometer 360 comprises: a specimen cell 6; a light source unit 50 comprising a spectrometer 2 and a light source 1 for emitting measurement light; photodetector 12; a plurality of reflecting mirrors 3, 4, 5, 9 and 11; an enclosure 15 that does not allow light to pass through; an index signal generator 20; an analog/digital (A/D) converter 14; and a computer 330 that controls the overall ultraviolet-visible spectrophotometer 360.

The computer 330 comprises a CPU (controller) 331 and a memory (memory unit) 334 and is further connected to a display device 33 and an input device 32 comprising a keyboard, mouse and the like. To explain the functional blocks of the CPU 331, CPU 331 comprises a memory controller 331a for storing in memory 334 the output strength signal from a photodetector 12 and a computation controller 331b for calculating transmittance.

Here, equation (1) and equation (21) and correction coefficients $A\lambda$ ($A\lambda 1$, $A\lambda 2$, $A\lambda 3$, . . . ) are stored in advance in memory 334.

$$s_N = (S_N - S_{N-1} \times A\lambda) \qquad (1)$$

$$\text{Transmittance (\%)} = s_N/Z \times 100 \qquad (21)$$

Z is the value of $s_N$ stored in advance that was obtained by the measurement of a specimen (oftentimes water or air) used as control.

The correction coefficient $A\lambda$ is a numerical value that is determined in advance either experimentally or computationally for each wavelength $\lambda 1$, $\lambda 2$, $\lambda 3$, . . . for eliminating the effects of output strength signal $S_{N-1}$ of incidence duration of the $(N-1)^{th}$ period that are included in output strength signal $S_N$ of the incidence duration of the $N^{th}$ period. For example, for each wavelength $\lambda 1$, $\lambda 2$, $\lambda 3$, . . . , the correction coefficient $A\lambda$ can be determined experimentally by measuring multiple times the change in output strength signal after the incidence of light to photodetector 12 and obtaining an average.

Computation controller 331b performs the control that uses equation (1) and equation (21) and correction coefficients $A\lambda 1$, $A\lambda 2$, $A\lambda 3$, . . . to calculate transmittance.

Specifically, wavelength $\lambda$ of the measurement light that was extracted by spectrometer 2 is acquired, and the average value of detection value data corresponding to output strength signal $S_{N-1}$ in the $(N-1)^{th}$ period is calculated. Furthermore, in the $N^{th}$ period, the average value is calculated for detection value data corresponding to output strength signal $S_N$. The average value is substituted into equation (1), and the true output strength signal $s_N$ is determined for the $N^{th}$ period. Then, the true output strength signal $s_N$ for the $N^{th}$ period is substituted into equation (21) to determine the transmittance for the $N^{th}$ period. In this way, the transmittance for the $N^{th}$ period is successively determined.

In the foregoing way, ultraviolet-visible spectrophotometer 360 eliminates the effects of output strength signal $S_{N-1}$ of the incidence duration of the $(N-1)^{th}$ period that are included in the output strength signal $S_N$ of the incidence duration of the $N^{th}$ period, thereby improving the measurement accuracy.

Fourth Embodiment

Figure 10:
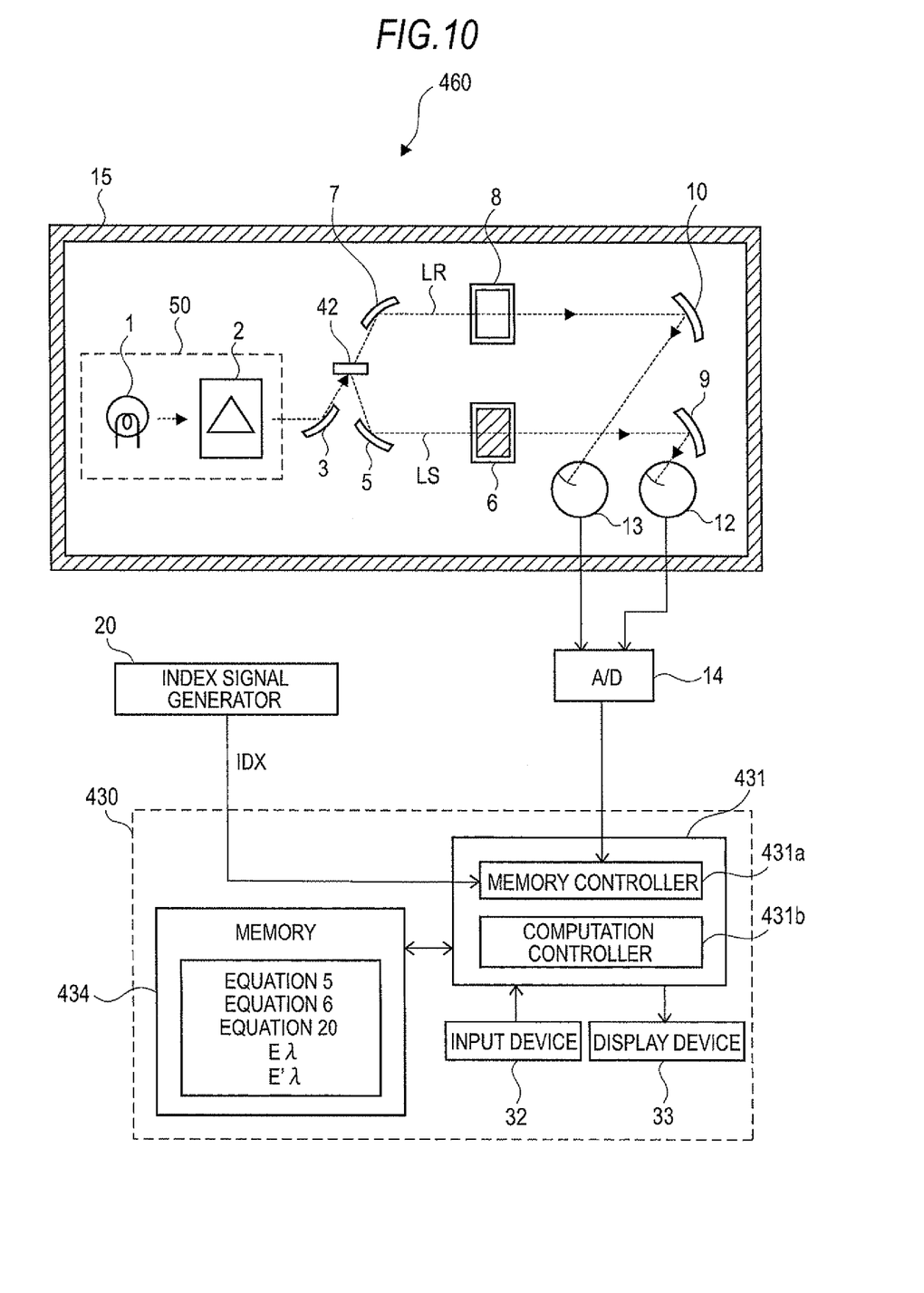
FIG. 10 shows a schematic view of the configuration of a double-beam type ultraviolet-visible spectrophotometer as a fourth embodiment of the present invention.

FIG. 10 shows a schematic view of the configuration of a fourth embodiment of the present invention as a double-beam type ultraviolet-visible spectrophotometer that does not have predetermined alternating periods of incidence duration and light-blocked duration. The same numerical references are used for the same components as in ultraviolet-visible spectrophotometer 160.

The ultraviolet-visible spectrophotometer 460 comprises: a specimen cell 6; a reference cell 8; a light source unit 50 comprising a spectrometer 2 and a light source 1 for emitting measurement light; a first photodetector 12; a second photodetector 13; light beam splitting half-mirror (splitter) 42; a plurality of reflecting mirrors 3, 5, 9 and 10; an enclosure 15 that does not allow light to pass through; an index signal generator 20; an analog/digital (A/D) converter 14; and a computer 430 that controls the overall ultraviolet-visible spectrophotometer 460.

Half-mirror 42 splits the light quantity of the measurement light into two equal parts for the specimen-side and the reference-side. The specimen-side light beam LS is continuously incident to first photodetector 12. The reference-side light beam LR is continuously incident to second photodetector 13. From the perspective of the respective photodetectors 12 and 13, they behave in the same manner as photodetectors in a single-beam type spectrophotometer without predetermined alternating periods of incidence duration and light-blocked duration.

The computer 430 comprises a CPU (controller) 431 and a memory (memory unit) 434 and is further connected to a display device 33 and an input device 32 comprising a keyboard, mouse and the like. To explain the functional blocks of the CPU 431, CPU 431 comprises a memory controller 431a for storing in memory 434 the output strength signal from a photodetector 12 and a computation controller 431b for calculating transmittance.

Here, equation (5), equation (6), equation (20) and correction coefficients E$\lambda$ (E$\lambda$1, E$\lambda$2, E$\lambda$3, . . . ) and correction coefficients E'$\lambda$ (E'$\lambda$1, E'$\lambda$2, E'$\lambda$3, . . . ) are stored in advance in memory 434.

$$s_N = (S_N - S_{N-1} \times E\lambda) \quad (5)$$

$$r_N = (R_N - R_{N-1} \times E'\lambda) \quad (6)$$

$$\text{Transmittance (\%)} = (s_N/r_N)/Z \times 100 \quad (20)$$

Z is the value of $(s_N/r_N)$ stored in advance that was obtained by the measurement of a specimen (oftentimes water or air) used as control.

The correction coefficient E$\lambda$ is a numerical value that is determined in advance either experimentally or computationally for each wavelength $\lambda$1, $\lambda$2, $\lambda$3, . . . for eliminating the effects of specimen-side output strength signal $S_{N-1}$ of incidence duration of the $(N-1)^{th}$ period that are included in specimen-side output strength signal $S_N$ of the incidence duration of the $N^{th}$ period. For example, for each wavelength $\lambda$1, $\lambda$2, $\lambda$3, . . . , the correction coefficient E$\lambda$ can be determined experimentally by measuring multiple times the change in output strength signal after the incidence of light to first photodetector 12 and obtaining an average.

The correction coefficient E'$\lambda$ is a numerical value that is determined in advance either experimentally or computationally for each wavelength $\lambda$1, $\lambda$2, $\lambda$3, . . . for eliminating the effects of reference-side output strength signal $R_{N-1}$ of incidence duration of the $(N-1)^{th}$ period that are included in reference-side output strength signal $R_N$ of the incidence duration of the $N^{th}$ period. For example, for each wavelength $\lambda$1, $\lambda$2, $\lambda$3, . . . , the correction coefficient E'$\lambda$ can be determined experimentally by measuring multiple times the change in output strength signal after the incidence of light to second photodetector 13 and obtaining an average.

Computation controller 431b performs the control that uses equation (5), equation (6), equation (20), correction coefficients E$\lambda$1, E$\lambda$2, E$\lambda$3, . . . and correction coefficients E'$\lambda$1, E'$\lambda$2, E'$\lambda$3, . . . to calculate transmittance.

Specifically, wavelength $\lambda$ of the measurement light that was extracted by spectrometer 2 is acquired, and the average value of detection value data corresponding to specimen-side output strength signal $S_{N-1}$ in the $(N-1)^{th}$ period and the average value of detection value data corresponding to specimen-side output strength signal $S_N$ in the $N^{th}$ period are calculated. The average values are substituted into equation (5), and the true specimen-side output strength signal $s_N$ is determined for the $N^{th}$ period. Furthermore, the average value of detection value data corresponding to reference-side output strength signal $R_{N-1}$ in the $(N-1)^{th}$ period and the average value of detection value data corresponding to reference-side output strength signal $R_N$ in the $N^{th}$ period are calculated. The average values are substituted into equation (6), and the true reference-side output strength signal $r_N$ is determined for the $N^{th}$ period. Then, the true specimen-side output strength signal $s_N$ and the true reference-side output strength signal $r_N$ for the $N^{th}$ period are substituted into equation (20) to determine the transmittance for the $N^{th}$ period. In this way, the transmittance for the $N^{th}$ period is successively determined.

In the foregoing way, ultraviolet-visible spectrophotometer 460 eliminates the effects of specimen-side output strength signal $S_{N-1}$ of the incidence duration of the $(N-1)^{th}$ period that are included in the specimen-side output strength signal $S_N$ of the incidence duration of the $N^{th}$ period and also eliminates the effects of reference-side output strength signal $R_{N-1}$ of the incidence duration of the $(N-1)^{th}$ period that are included in the reference-side output strength signal $R_N$ of the incidence duration of the $N^{th}$ period, thereby improving the measurement accuracy.

Other Embodiments (1) With the afore-described ultraviolet-visible spectrophotometer 60, equation (7), equation (8), equation (20) and correction coefficient F$\lambda$1, F$\lambda$2, F$\lambda$3, . . . are stored in advance in memory 34. Computation controller 31b uses equation (7), equation (8), equation (20) and correction coefficients F$\lambda$1, F$\lambda$2, F$\lambda$3, . . . to calculate transmittance. However, it is also possible to store equation (9), equation (10), equation (20) and correction coefficients F$\lambda$1, F$\lambda$2, F$\lambda$3, . . . and G$\lambda$1, G$\lambda$2, G$\lambda$3, . . . in the memory in advance, and for the computation controller to use equation (9), equation (10), equation (20) and correction coefficients F$\lambda$1, F$\lambda$2, F$\lambda$3, . . . and G$\lambda$1, G$\lambda$2, G$\lambda$3, . . . to calculate transmittance. It is also possible to store equation (11), equation (12), equation (20) and correction coefficients H$\lambda$1, H$\lambda$2, E$\lambda$3, . . . in the memory in advance and for the computation controller to use equation (11), equation (12), equation (20) and correction coefficients H$\lambda$1, H$\lambda$2, H$\lambda$3, . . . to calculate transmittance. It is also possible to store equations (7) through (12), equation (20) and correction coefficients in the memory in advance and for the computation controller to select equations (7) through (12), equation (20) and correction coefficients to calculate transmittance.

$$s_N=(S_N-R_{N-1}\times F)-(DS_N-S_N\times G) \quad (9)$$

$$r_N=(R_N-S_N\times F)-(DR_N-R_N\times G) \quad (10)$$

$$s_N=S_N-(DR_{N-1}-DS_N)\times\frac{1}{2}\times H-DS_N \quad (11)$$

$$r_N=R_N-(DS_N-DR_N)\times\frac{1}{2}\times H-DR_N \quad (12)$$

If equation (11) is used for the first period, equation (11') may be used instead.

If equation (9) is used for the first period, equation (9') may be used instead.

$$s_N=S_N-(DR_N-DS_N)\times\frac{1}{2}\times H-DS_N \quad (11')$$

$$s_N=(S_N-R_N\times F)-(DS_N-S_N\times G) \quad (9')$$

(2) With the afore-described ultraviolet-visible spectrophotometer 260, equation (4), equation (21) and correction coefficients Dλ1, Dλ2, Dλ3, . . . are stored in advance in memory 234, and computation controller 231b uses equation (4), equation (21) and correction coefficients Dλ1, Dλ2, Dλ3, . . . to calculate transmittance. However, it is also possible to store equation (3), equation (21) and correction coefficients Bλ1, Bλ2, Bλ3 . . . and Cλ1, Cλ2, Cλ3, . . . in advance in the memory and for the computation controller to use equation (3), equation (21) and correction coefficients Bλ1, Bλ2, Bλ3, . . . and Cλ1, Cλ2, Cλ3, . . . to calculate transmittance. It is also possible to store equation (2), equation (21) and correction coefficients Bλ1, Bλ2, Bλ3, . . . in advance in the memory and for the computation controller to use equation (2), equation (21) and correction coefficients Bλ1, Bλ2, Bλ3, . . . to calculate transmittance. Equations (1) through (4), equation (21) and correction coefficients can be stored in advance in the memory, and the computation controller can select equations (1) through (4), equation (21) and correction coefficients to calculate transmittance.

$$s_N=(S_N-S_{N-1}\times B)-(DS_N-S_N\times C) \quad (3)$$

$$s_N=(S_N-S_{N-1}\times B)-DS_N \quad (2)$$

(3) The afore-described ultraviolet-visible spectrophotometer 60 was configured with computer 30 being disposed at a separate location from enclosure 15, but the computer can also be configured integrally with the enclosure.

INDUSTRIAL USABILITY

The present invention can be used, for example, with double-beam type and single-beam type ultraviolet-visible spectrophotometers and the like.

DESCRIPTION OF THE NUMERICAL REFERENCES

6. Specimen cell
12. Photodetector
41. Light-shielding unit
50. Light source unit
31, 231. CPU (controller)
34, 234. Memory (memory unit)
60, 260. Ultraviolet and visible spectrophotometer

What is claimed is:

1. A spectrophotometer comprising:
    a specimen cell;
    a light source unit for emitting measurement light to said specimen cell;
    a photodetector for detecting measurement light that has passed through said specimen cell;
    a memory unit for storing output strength signals obtained by said photodetector; and
    a control unit for calculating transmittance or absorbance based on the output strength signal (S) that is stored in said memory unit; wherein:
    said controller calculates the true output strength signal ($s_N$) of the $N^{th}$ period removed of the effects of output strength signals ($S_{N-1}$, $S_{N-2}$, $S_{N-3}$, . . . ) of the incidence duration of the $(N-1)^{th}$ period and earlier that are included in the output strength signal ($S_N$) of the incidence duration of the $N^{th}$ period.

2. The spectrophotometer according to claim 1 wherein said memory unit stores correction coefficient A for eliminating the effects of output strength signal ($S_{N-1}$) of the incidence duration of the $(N-1)^{th}$ period that are included in the output strength signal ($S_N$) of the incidence duration of the $N^{th}$ period and said controller uses equation (1) below to calculate the true output strength signal ($s_N$) of the $N^{th}$ period:

$$s_N=(S_N-S_{N-1}\times A). \quad (1)$$

3. The spectrophotometer according to claim 1 further comprising a light-shielding unit for preventing the incidence of measurement light from said light source unit onto the photodetector for predetermined periods so that an incidence duration and light-blocked duration occur in this sequence in a single period; wherein:
    said memory unit stores the output strength signal obtained by said photodetector in association with the light-blocked duration when light is blocked by said light-shielding unit; and
    said controller calculates transmittance or absorbance based on output strength signal (S) of the incidence duration and output strength signal (DS) of the light-blocked duration that are stored in said memory unit.

4. The spectrophotometer according to claim 3 wherein said memory unit stores correction coefficient B for eliminating the effects of output strength signal ($S_{N-1}$) of the incidence duration of the $(N-1)^{th}$ period that are included in the output strength signal ($S_N$) of the incidence duration of the $N^{th}$ period and said controller uses equation (2) below to calculate the true output strength signal ($s_N$) of the $N^{th}$ period:

$$s_N=(S_N-S_{N-1}\times B)-DS_N. \quad (2)$$

5. The spectrophotometer according to claim 3 wherein said memory unit stores correction coefficient B for eliminating the effects of output strength signal ($S_{N-1}$) of the incidence duration of the $(N-1)^{th}$ period that are included in the output strength signal ($S_N$) of the incidence duration of the $N^{th}$ period and correction coefficient C for eliminating the effects of output strength signal ($S_N$) of the incidence duration of the $N^{th}$ period that are included in the output strength signal ($DS_N$) of the light-blocked duration of the $N^{th}$ period and said controller uses equation (3) below to calculate the true output strength signal ($s_N$) of the $N^{th}$ period:

$$s_N=(S_N-S_{N-1}\times B)-(DS_N-S_N\times C). \quad (3)$$

6. The spectrophotometer according to claim 3 wherein said memory unit stores correction coefficient D for eliminating the effects of output strength signal ($S_{N-1}$) of the incidence duration of the $(N-1)^{th}$ period that are included in the output strength signal ($S_N$) of the incidence duration of the $N^{th}$ period and said controller uses equation (4) below to calculate the true output strength signal ($s_N$) of the $N^{th}$ period:

$$s_N=S_N-(DS_{N-1}-DS_N)\times\frac{1}{2}\times D-DS_N. \quad (4)$$

7. The spectrophotometer according to claim 1 further comprising:
a reference cell;
a second photodetector for detecting the measurement light that has passed through said reference cell; and
a splitter for splitting the measurement light to said specimen cell and said reference cell; wherein:
said memory unit stores the output strength signal obtained by said second photodetector;
said controller calculates transmittance or absorbance based on specimen-side output strength signal (S) and reference-side output strength signal (R) that are stored in said memory unit; and
said controller calculates true reference-side output strength signal ($r_N$) of the $N^{th}$ period removed of the effects of the output strength signal ($R_{N-1}$, $R_{N-2}$, $R_{N-3}$, ...) of the reference-side incidence duration of the $(N-1)^{th}$ period and earlier included in the output strength signal ($R_N$) of the reference-side incidence duration of the $N^{th}$ period.

8. The spectrophotometer according to claim 7 wherein said memory unit stores correction coefficient E for eliminating the effects of the output strength signal ($S_{N-1}$) of the specimen-side incidence duration of the $(N-1)^{th}$ period that are included in the output strength signal ($S_N$) of the specimen-side incidence duration of the $N^{th}$ period, correction coefficient E' for eliminating the effects of the output strength signal ($R_{N-1}$) of the reference-side incidence duration of the $(N-1)^{th}$ period that are included in the output strength signal ($R_N$) of the reference-side incidence duration of the $N^{th}$ period and said controller uses equation (5) below to calculate the true output strength signal ($s_N$) of the $N^{th}$ period and uses equation (6) below to calculate the true reference-side output strength signal ($r_N$) of the $N^{th}$ period:

$$s_N = (S_N - S_{N-1} \times E) \tag{5}$$

$$r_N = (R_N - R_{N-1} \times E'). \tag{6}$$

9. A spectrophotometer comprising:
a specimen cell;
a light source unit for emitting measurement light to said specimen cell;
a photodetector for detecting the measurement light that has passed through said specimen cell;
a light-shielding unit for preventing the incidence of the measurement light from said light source unit to the photodetector at predetermined periods;
a reference cell;
a switching unit for switchably guiding the measurement light to the reference cell instead of said specimen cell at predetermined periods;
a memory unit for storing the output strength signals detected by said photodetector in association with a light-blocked duration when light is blocked by said light-shielding unit and switched duration when the optical path is switched by said switching unit; and
a controller for calculating transmittance or absorbance based on output strength signal (S) of the specimen-side incidence duration, output strength signal (DS) of the specimen-side light-blocked duration, output strength signal (R) of the reference-side incidence duration and output strength signal (DR) of the reference-side light-blocked duration that are stored in said memory unit; wherein:
the specimen-side incidence duration, specimen-side light-blocked duration, reference-side incidence duration and reference-side light-blocked duration occur in this sequence in a single period; and
said controller calculates the true specimen-side output strength signal ($s_N$) of the $N^{th}$ period removed of the effects of output strength signal ($R_{N-1}$, $S_{N-1}$, $R_{N-2}$, $S_{N-2}$, ...) prior to the reference-side incidence duration of the $(N-1)^{th}$ period that are included in the output strength signal ($S_N$) of the specimen-side incidence duration of the $N^{th}$ period and calculates the true reference-side output strength signal ($r_N$) of the $N^{th}$ period removed of the effects of output strength signal ($S_N$, $R_{N-1}$, $S_{N-1}$, $R_{N-2}$, ...) prior to the specimen-side incidence duration of the $N^{th}$ period that are included in the output strength signal ($R_N$) of the reference-side incidence duration of the $N^{th}$ period.

10. The spectrophotometer according to claim 9 wherein said memory unit stores correction coefficient F for eliminating the effects of the output strength signal ($R_{N-1}$) of the reference-side incidence duration of the $(N-1)^{th}$ period that are included in the output strength signal ($S_N$) of the specimen-side incidence duration of the $N^{th}$ period, correction coefficient F' for eliminating the effects of the output strength signal ($S_N$) of the specimen-side incidence duration of the $N^{th}$ period that are included in the output strength signal ($R_N$) of the reference-side incidence duration of the $N^{th}$ period and said controller uses equation (7) below to calculate the true specimen-side output strength signal ($s_N$) of the $N^{th}$ period and uses equation (8) below to calculate the true reference-side output strength signal ($r_N$) of the $N^{th}$ period:

$$s_N = (S_N - R_{N-1} \times F) - DS_N \tag{7}$$

$$r_N = (R_N - S_N \times F') - DR_N. \tag{8}$$

11. The spectrophotometer according to claim 9 wherein said memory unit stores correction coefficient F for eliminating the effects of the output strength signal ($R_{N-1}$) of the reference-side incidence duration of the $(N-1)^{th}$ period that are included in the output strength signal ($S_N$) of the specimen-side incidence duration of the $N^{th}$ period, correction coefficient F' for eliminating the effects of the output strength signal ($S_N$) of the specimen-side incidence duration of the $N^{th}$ period that are included in the output strength signal ($R_N$) of the reference-side incidence duration of the $N^{th}$ period, correction coefficient G for eliminating the effects of the output strength signal ($S_N$) of the specimen-side incidence duration of the $N^{th}$ period that are included in the output strength signal ($DS_N$) of the specimen-side light-blocked duration of the $N^{th}$ period, correction coefficient G' for eliminating the effects of the output strength signal ($R_N$) of the reference-side incidence duration of the $N^{th}$ period that are included in the output strength signal ($DR_N$) of the reference-side light-blocked duration of the $N^{th}$ period and said controller uses equation (9) below to calculate the true specimen-side output strength signal ($s_N$) of the $N^{th}$ period and uses equation (10) below to calculate the true reference-side output strength signal ($r_N$) of the $N^{th}$ period:

$$s_N = (S_N - R_{N-1} \times F) - (DS_N - S_N \times G) \tag{9}$$

$$r_N = (R_N - S_N \times F') - (DR_N - R_N \times G'). \tag{10}$$

12. The spectrophotometer according to claim 9 wherein said memory unit stores correction coefficient H for eliminating the effects of the output strength signal ($R_{N-1}$) of the reference-side incidence duration of the $(N-1)^{th}$ period that are included in the output strength signal ($S_N$) of the specimen-side incidence duration of the $N^{th}$ period, correction coefficient H' for eliminating the effects of the output strength signal ($S_N$) of the specimen-side incidence duration of the $N^{th}$ period that are included in the output strength signal ($R_N$) of the reference-side incidence duration of the $N^{th}$ period, and said controller uses equation (11) below to calculate the true specimen-side output strength signal ($s_N$) of the $N^{th}$ period and uses equation (12) below to calculate the true reference-side output strength signal ($r_N$) of the $N^{th}$ period:

$$s_N = S_N - (DR_{N-1} - DS_N) \times \tfrac{1}{2} \times H - DS_N \quad (11)$$

$$r_N = R_N - (DS_N - DR_N) \times \tfrac{1}{2} \times H' - DR_N. \quad (12)$$

\* \* \* \* \*